(12) United States Patent
Chang et al.

(10) Patent No.: US 6,197,344 B1
(45) Date of Patent: Mar. 6, 2001

(54) BUTORPHANOL SUSTAINED RELEASE FORMULATIONS

(75) Inventors: Hung-Chih Chang, Gurnee; Lukchiu Li, Vernon Hills; Youqin Tian, Mundelein, all of IL (US)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 09/429,391

(22) Filed: Oct. 28, 1999

Related U.S. Application Data

(63) Continuation of application No. 09/030,217, filed on Feb. 25, 1998, now abandoned.

(51) Int. Cl.[7] .................................................. A61K 9/14
(52) U.S. Cl. .................. 424/489; 424/422; 514/282; 514/289; 514/938; 514/964
(58) Field of Search .................. 514/282, 289, 514/938, 964; 424/422, 489

(56) References Cited

U.S. PATENT DOCUMENTS

| | | | |
|---|---|---|---|
| 3,819,635 | 6/1974 | Pachter et al. ................ | 260/285 |
| 4,322,427 | 3/1982 | Buyniski et al. .............. | 424/460 |
| 4,338,324 | 7/1982 | Gardocki et al. .............. | 424/266 |
| 4,464,378 | 8/1984 | Hussain ........................ | 424/260 |
| 5,629,011 | * 5/1997 | Illum ........................... | 424/434 |
| 5,672,360 | * 9/1997 | Sackler et al. ................ | 424/490 |
| 5,748,577 | 5/1998 | Sackler et al. ................ | 424/489 |

FOREIGN PATENT DOCUMENTS

| | | |
|---|---|---|
| 0300806 | 1/1989 | (EP) . |
| 9414426 | 7/1994 | (WO) . |
| 9624330 | 8/1996 | (WO) . |
| 91/4549 | 6/1991 | (ZA) . |

OTHER PUBLICATIONS

H.C. Chang, et al., "Parenteral Sustained–Release Dosage Forms of Butorphanol For Dogs", *International Journal of Pharmaceutics*, vol. 176, No.2, (1999), 147–156.

M. Pfeffer, et al., "Pharmacokinetics of Subcutaneous and Intramuscular Butorphanol in Dogs", *Journal of Pharmaceutical Sciences*, vol. 69, No. 7 (Jul. 1980), 801–803.

"Handbook of Pharmaceutical Excipients"; American Pharmaceutical Association Production Staff, James C. Boylan, Jack Cooper and Zak T. Chowhan and the Pharmaceutical Society of Great Britain Production Staff, walter Lund, Ainley wade, Robert F. Weir and Bernard J. Yates; Copyright 1986.

* cited by examiner

Primary Examiner—Thurman K. Page
Assistant Examiner—Lakshmi Channavajjala
(74) Attorney, Agent, or Firm—Gregory W. Steele

(57) ABSTRACT

Controlled, sustained release formulations of butorphanol are provided. Such formulations can be an aqueous suspension of butorphanol freebase or an oil suspension of a butorphanol salt. Processes for using such formulations to provide long term analgesia are also provided.

30 Claims, No Drawings

BUTORPHANOL SUSTAINED RELEASE FORMULATIONS

RELATED APPLICATIONS

This application is a continuation of U.S. application Ser. No. 09/030,217, filed Feb. 25, 1998, incorporated herein by reference, now abandoned.

TECHNICAL FIELD OF THE INVENTION

The field of this invention is long-term pain management. More particularly, the present invention relates to controlled release formulations of the opioid analgesic, butorphanol, and the use of such formulations for pain management over periods of time ranging from 12 to 24 hours.

BACKGROUND OF THE INVENTION

Butorphanol is a synthetic opioid agonist-antagonist that is highly effective for the treatment of both chronic and acute pain. Parenterally administered butorphanol is more potent than morphine and most other morphine analogs. Butorphanol is metabolized in the liver and excreted by the kidney. The elimination of butorphanol and its metabolites is rapid and the duration of analgesia is usually in the range of three to four hours, with maximal analgesia obtained one-half to one hour following parenteral administration. Butorphanol can be used to treat acute surgical pain, severe post-operative pain and chronic pain. The drug has been shown to be an effective pain management therapy in treating pain associated with numerous types of surgery, burns and kidney stones.

Parenteral formulations of butorphanol and the use of parenteral butorphanol for the relief of acute and chronic pain are known in the art (See, e.g., U.S. Pat. No. 3,819,635). A parenteral formulation of butorphanol is commercially available under the name STADOL® from Bristol-Meyers Laboratories, Inc. 2–4 mg of that formulation are typically injected intramuscularly for the treatment of post-operative pain. Typically, dosing interval ranges from about three to about four hours are needed to sustain analgesia.

A sustained release formulation of butorphanol encapsulated in phospholipid vesicles or Liposome is disclosed in European Patent Application 0300806A1. In accordance with that disclosure, butorphanol tartrate in phosphate buffered saline is encapsulated with lipid films of distearoylphosphatidylcholine and cholesterol. Effective levels of analgesia ranging from 12 to about 24 hours can be achieved by administering such Liposome encapsulated butorphanol.

South African Patent Application 91/4549 discloses sustained release pharmaceutical formulations and the use of those formulations in delivering therapeutic agents over periods of time of from about 12 to about 24 hours. Formulations disclosed in that South African patent application are microspheres of between 5 to 300 micrometers that contain at least one pharmaceutically active substance contained in a spherical structure formed by at least one pharmacologically inactive carrier substance. The carrier substance is naturally present in the organism to be treated and is stable in the solid state up to a temperature of at least 60° C. Exemplary such carrier substances are coprosterol, glycocholic acid, cholesterol and cholesterol esters. Pharmaceutically active substances that can be administered using such micro spheres are tranquilizers, anti-emetics, vasodilators, antihistiminics, steroids and analgesics.

Existing sustained release formulations are costly and require multi-step manufacturing procedures. There continues to be a need in the art for simple, inexpensive formulations of butorphanol that provide a controlled, sustained release of the drug over long periods of time.

BRIEF SUMMARY OF THE INVENTION

In one aspect, the present invention provides a pharmaceutical composition for the controlled release of butorphanol. The composition contains an effective therapeutic amount of butorphanol free base suspended in an aqueous buffer having a pH less than about 7.0. In a preferred embodiment, the pH is from about 6.2 to about 6.5 and, more preferably from about 6.2 to about 6.3. The composition is preferably in the form of microparticles having an average diameter of from about 5 to about 25 microns. Preferably, the sizes of the microparticles are from about 5 to about 15 microns.

The aqueous composition can contain a wide range of effective butorphanol concentrations. A particularly suitable concentration range is from about 4 to about 10 mg/ml and, preferably from about 5 to about 7.5 mg/ml.

An aqueous composition of this invention can further include an effective amount of a non-ionic solubilizing agent. Exemplary and preferred such solubilizing agents are polyoxyethylene sorbitan fatty acid esters such as polysorbate 80. The composition can still further include an effective amount of a preservative. A preferred preservative is an alkylparaben such as methylparaben or propylparaben.

In another aspect, the present invention provides a pharmaceutical composition for the controlled release of butorphanol, which composition includes an effective therapeutic amount of a butorphanol salt suspended in oil. A preferred butorphanol salt for use in such a composition is butorphanol tartrate.

In a preferred embodiment, butorphanol is present in such a composition in a concentration range of from about 5 to about 30 mg/ml and, more preferably from about 10 to about 20 mg/ml. Any GRAS oil known in the pharmaceutical art can be used in the composition. Exemplary and preferred such oils are cottonseed oil, corn oil, peanut oil, sesame oil and soybean oil. Soybean oil is most preferred.

The oil-based composition can further include an effective amount of a suspending agent or emulsifier. A preferred suspending agent is a sorbitan fatty acid ester such as a sorbitan mono-, di- or tri-laurate, a sorbitan mono-, di- or tri-oleate, a sorbitan mono-, di- or tri-palmitate, or a sorbitan mono-, di- or tri-stearate. An especially preferred sorbitan fatty acid ester is span 85.

Either the aqueous- or oil-based composition can be used to provide effective long-term pain management in patients. The injection of an effective therapeutic amount of either composition provides effective pain management over a period of time of about 12 to about 24 hours and preferably over a time period of 18 to 24 hours. Effective long-term pain management is accomplished by injecting an amount of either composition sufficient to maintain plasma butorphanol concentration at a level of between about 20 and 100 ng/ml.

DETAILED DESCRIPTION OF THE INVENTION

I. The Invention

Pharmaceutical compositions for the controlled, sustained release of an opioid analgesic are provided. The composition can be formulated either as an aqueous- or an oil based formulation. Injection of a composition of this invention has use in providing long-term pain management in patients in need of such therapy.

II. Aqueous Formulation

In one embodiment, a composition of this invention is an aqueous suspension of butorphanol. Butorphanol is an art recognized pain relieving agent that belongs to the class of analgesics known as synthetic opioid agonists-antagonists. Butorphanol can exist either as a free base or as a salt. For use in an aqueous formulation of the present invention, the free base form is used. As is known in the art, the free base can be made by titrating a butorphanol salt (e.g., butorphanol tartrate) with an alkali metal salt such as NaOH.

The composition contains an effective therapeutic amount of butorphanol free base suspended in a buffered aqueous medium. The $pK_a$ of butorphanol is 8.6. The solubility of butorphanol is inversely proportional to pH over the pH range of 6.0 to 8.5. By way of example, at a pH of about 6.25, about 60% of butorphanol is in solution whereas at a pH of about 7.0, only about 5% of the drug is in solution. As shown hereinafter in the Examples, however, formulations at either pH release virtually 100% of the drug over 48 hours. The initial rate of release of the drug is somewhat higher at low pH's. A preferred pH for an aqueous composition of the present invention is between about 6.0 and 7.5. More preferably, the pH is from about 6.25 to about 7.0. pH of the composition is maintained at the desired level through the use of pharmaceutically acceptable buffers such as sodium citrate or sodium phosphate.

The aqueous composition can be made to contain a wide range of effective butorphanol concentrations. The only limit on butorphanol levels is the solubility of the drug in the composition. A particularly suitable concentration range in a composition having a pH of between 6.0 and 7.5 is from about 4 to about 20 mg/ml. More preferably, the concentration of butorphanol is from about 5 to about 15 mg/ml.

The aqueous composition can include substances other than buffers and butorphanol. In one embodiment, the composition further includes an effective amount of a non-ionic solubilizing agent. Exemplary and preferred such solubilizing agents are polyoxyethylene sorbitan fatty acid esters such as polysorbate 80. Suitable levels of such solubilizing agents are well known in the art and depend inter alia on the particular solubilizer used. When the solubilizing agent is polysorbate 80, a suitable effective amount is from about 0.5 to about 2.0 weight percent.

The composition can still further include an effective amount of a preservative. Suitable preservatives for use in pharmaceutical compositions are well known in the art (See. e.g., Handbook of Pharmaceutical Excipients, published by the American Pharmaceutical Association and the Pharmaceutical Society of Great Britain). An exemplary and preferred preservative is an alkylparaben such as methylparaben or propylparaben. The preservative is typically present in the composition in a concentration range of from about 0.01 to about 0.4 mg/ml and, more preferably from about 0.02 to about 0.2 mg/ml.

The composition can be formulated as microparticles by passing the composition through a microfluidizer as is well known in the art. Preferred microparticles have an average diameter of from about 5 to about 25 microns. More preferably, the size of the microparticles is from about 5 to about 15 microns. A detailed description of the preparation and controlled release characteristics of aqueous butorphanol suspensions can be found hereinafter in the Examples.

III. Oil Formulation

A controlled release butorphanol composition can also be in the form of an oil suspension or an oil/water emulsion. In accordance with this embodiment, an effective therapeutic amount of a butorphanol salt is suspended in a pharmaceutically acceptable oil. A preferred butorphanol salt for use in such a composition is butorphanol tartrate.

In a preferred embodiment, butorphanol is present in such a composition in a concentration range of from about 5 to about 30 mg/ml and, more preferably from about 10 to about 20 mg/ml. Any GRAS oil known in the pharmaceutical art can be used in the composition. Exemplary and preferred such oils are cottonseed oil, corn oil, peanut oil, sesame oil and soybean oil. Soybean oil is most preferred.

The oil-based composition can further include an effective amount of a suspending agent. A preferred such suspending agent is a sorbitan fatty acid hexitan ester such as a sorbitan mono-, di- or tri-laurate, a sorbitan mono-, di- or tri-oleate, a sorbitan mono-, di- or tri-palmitate, or a sorbitan mono-, di- or tri-stearate. An especially preferred sorbitan fatty acid ester is commercially available as Span 85. The suspending agent is typically present in a concentration of from about 0.5 percent (w/v) to about 2.0 percent (w/v).

IV. Process of Pain Management

Either the aqueous- or oil-based composition can be used to provide effective long-term pain management in patients. The injection of an effective therapeutic amount of either composition provides effective pain management over a period of time of about 12 to about 24 hours and preferably over a time period of 18 to 24 hours. Effective long-term pain management is accomplished by injecting an amount of either composition sufficient to maintain plasma butorphanol concentration at a level of between about 20 and 100 ng/ml.

The Examples that follow illustrate particular embodiments of the present invention and are not limiting of the specification and claims in any way.

EXAMPLE 1

Preparation of Butorphanol Formulations

A. Preparation of the Aqueous Suspensions

In the preparation of the aqueous suspensions, butorphanol tartrate was used as the starting material and the free base was produced in-situ by neutralizing the salt with a base solution. Two aqueous suspensions have been prepared and evaluated.

i. 5 mg/mL Aqueous Suspension

TABLE 1

Formulation of the 5 mg/mL Aqueous Suspension

| Ingredient | Amount |
| --- | --- |
| Butorphanol Tartrate | 1.0 g |
| Tween 80 | 1.0 g |
| Phosphate Buffer (0.2 M) | 140.0 g |
| Methylparaben | 40 mg |
| Propylparaben | 4.0 mg |
| 1 N NaOH | 24 g |
| Water for Injection | q.s. to 200 mL |

In brief, 40 mg methylparaben, 4 mg propylparaben, and 1 g Tween 80 were dissolved in 140 g phosphate buffer by heating the mixture to ~55° C. One gram of butorphanol tartrate was dissolved into the solution. To produce butorphanol free base, sodium hydroxide (NaOH) was then added dropwise into the solution mixture containing the drug under agitation, using the Silverson high-shear mixer at 7,000 rpm for five minutes. Water for injection was added to make a final volume of 200 mL. The pH of the suspension was 6.25. The resulting suspension was passed through the Microfluidizer 110Y (Microfluidics, Newton, Mass.) for 10 cycles with the 75-µm interaction chamber and the 200 µm backpressure module at 12,000 psi. The drug particle size has been estimated, by visual examination under an optical microscope, to be in the range of 5–10 μm.

ii. 10 mg/mL Aqueous Suspension

TABLE 2

Formulation of the 10 mg/mL Aqueous Suspension

| Ingredient | Amount |
|---|---|
| Butorphanol Tartrate | 2.0 g |
| Tween 80 | 1.0 g |
| Citrate Buffer (0.2 M) | 120.0 g |
| 1 N NaOH | 61 g |
| 0.1 N NaOH | 5.0 g |
| Water for Injection | q.s. to 200 mL |

In this formulation, preparation procedures similar to those for the 5 mg/mL suspension were employed. One gram of Tween 80™ was dissolved in 120 g citrate buffer by heating the mixture to ~55° C. Then, 1 g of butorphanol tartrate was dissolved into this solution. To produce butorphanol free base, sodium hydroxide was added dropwise into the solution mixture containing the drug under agitation, using the Silverson high-shear mixer at 7,000 rpm for five minutes. Water for injection was added to make a final volume of 200 mL. In the resulting suspension, the pH was 7.00 and the particle size has been estimated, by visual examination under an optical microscope, to be between 30 and 40 μm.

B. Preparation of the Oil Suspension

Two oil suspensions were prepared and evaluated (Tables 3 and 4).

TABLE 3

Formulation of the 20 mg/mL Oil Suspension

| Ingredient | Amount |
|---|---|
| Butorphanol Tartrate | 2 g |
| Span 85 | 1 g |
| Soybean Oil | q.s. to 100 mL |

TABLE 4

Formulation of the 10 mg/mL Oil suspension

| Ingredient | Amount |
|---|---|
| Butorphanol Tartrate | 1 g |
| Span 85 | 1 g |
| Soybean Oil | q.s. to 100 mL |

To prepare the oil suspension, a predetermined amount of spray-dried butorphanol tartrate (2–10 μm) was placed in a beaker and a predetermined amount of a suspending agent (Span 85) was added and mixed with the drug until a smooth paste was formed. Oil was subsequently added in small portions with continuous stirring until the required volume was achieved. The final product was mixed using a Silverson® high-shear mixer for five minutes at 5,000 rpm and was stored at room temperature for further evaluation.

C. Analysis of the Butorphanol Content in Formulations i. Aqueous Suspension

The drug content of selected butorphanol/aqueous suspensions was analyzed by HPLC assay: One mL of the aqueous suspension was pipetted into a 100 mL volumetric flask. Ten mL of 1N sulfuric acid was subsequently added to dissolve the drug. The volume was then made up to 100 mL with water and directly injected onto the HPLC. In order to determine the drug content in the solution phase, 3 mL of the suspension was filtered through a 0.22 μm filter. The filtrate was then directly injected onto the HPLC as described above.

The HPLC system consisted of a Model SIL-9A autoinjector (Shimadzu®), a Model SPD-6A UV-spectrophotometer (Shimadzu®), and a Model CR501 integrator (Shimadzu®). The stationary phase was a μBondapak™ Phenyl column (3.9×300 mm, Waters, USA). The mobile phase was prepared by mixing 1 L 0.05M ammonium acetate and 335 mL acetonitrile, with pH adjustment to 4.1 using glacial acetic acid. The chromatogram was monitored by UV detection at the maximum wavelength of 280 nm, with a sensitivity setting of 0.08 AUFS. The injection volume was 100 μL and the flow rate was 2 mL/min.

ii. Oil Suspension

The drug content of selected butorphanol tartrate/oil suspensions was analyzed by HPLC assay: One mL of the oil suspension was pipetted and placed in a centrifuge tube. Ten mL 1N sulfuric acid was added. The tubes were shaken using a Burell wrist-action shaker for a period of 15 minutes and then centrifuged for five minutes at 3000 rpm. The aqueous phase was separated from the oil phase and further diluted before being injected into the colum. In order to determine the amount of drug in the oil-solution phase, 3 mL of the oil suspension was filtered through a 0.22 μm filter. One mL of this filtrate was pipetted into a centrifuge tube and 10 mL 1N sulfuric acid was added to the tube, which was subsequently shaken and centrifuged as described above. The aqueous solution was sampled and injected directly onto the HPLC.

D. Evaluation of Butorphanol Release

A predetermined amount of aqueous or oil suspension was transferred, in duplicate, to dialysis tubing (Spectra®)/Por2, MWCO 12,000–14,000) and the tubing was placed in 100 mL of 0.1M phosphate buffer (pH 7.4) being used as dialyzate. Agitation was achieved using a magnetic stirrer at a speed of 600 rpm. At a predetermined sampling time interval, 1 mL of the dialyzate was withdrawn for content assay using the HPLC method as described above. To maintain the drug-release study under sink conditions, the residual dialyzate was discarded and replaced with fresh medium at each sampling time point.

The drug-release profiles for the 10 mg/mL and 20 mg/mL oil suspensions were similar. The total drug release was over 80% after 48 hours. The data also show that the drug dissolution rate did not slow down with a higher percentage of oil surrounding the drug particles. The drug-release profiles of butorphanol free base from aqueous suspensions with two different pHs and drug-particle sizes showed that the total cumulative drug releases from these two aqueous formulations were close to 100% after 48 hours. However, drug release in the first 24 hours was much faster in the 5 mg/mL suspension (pH 6.25) compared to that of the 10 mg/mL (pH 7.00). The faster release rate may be attributed to the higher solubility of the drug at this lower pH and the smaller drug-particle size.

EXAMPLE 2

In-vivo Evaluations of Formulations

A. Animal Study Design

Fifteen beagle dogs were obtained from the established Abbott-Drug Analysis Colony. The dogs were randomly assigned to one of the following five groups; each group contained three animals.

TABLE 5

Formulations Tested in Dogs

| Formulation | Concentration | Description |
|---|---|---|
| A | 5 mg/mL | Aqueous Suspension |
| B | 10 mg/mL | Aqueous Suspension |
| C | 10 mg/mL | Oil Suspension |
| D | 20 mg/mL | Oil Suspension |
| E | 2 mg/mL | Torbugesic-SA Injection |

The dogs received a 2 mg/kg subcutaneous dose of either one of the experimental suspension formulations or the reference immediate-release injection. Heparinized blood samples were obtained from a jugular vein of each dog prior to dosing and 0.25, 0.5, 1, 2, 4, 6, 9, 12, 15, 24, 48, and 72 hours after dosing. The plasma was separated from the red cells by centrifugation (2500 rpm/10 minutes, 4° C.) and frozen −20° C. for subsequent analysis.

B. Drug Analysis for Animal Study

Butorphanol and an internal standard were separated from the plasma matrix using liquid—liquid extraction with chloroform under alkaline conditions. Briefly, 0.5 mL plasma was mixed with 0.1 mL internal standard 1.0 mL 1N NaOH, and 7 mL chloroform. The samples were vortexed for 20 seconds, followed by centrifugation. The upper aqueous layer was aspirated to waste. The organic layer was transferred to a conical centrifuge tube and evaporated to dryness with a gently stream of dry air over low heat (~35° C.). The samples were reconstituted in 0.2 mL acetonitrile:water (3:7, by volume). Butorphanol plasma standards were analyzed simultaneously with the samples.

Butorphanol and the internal standard were separated from the co-extracted plasma contaminants on a 25 cm×4.6 mm ODS-AQ (YMC, Inc.) Column using an acetonitrile:methanol:buffer mobile phase (16:10:74, by volume) at a flow rate of 1.0 mL/min. The mobile-phase buffer was comprised of 0.05M potassium phosphate with 0.01M tetramethylammonium perchlorate, adjusted to pH 6.0 prior to being combined with the organic fractions. Electrochemical detection in the oxidative mode (DET1=+0.4V,DET2=+0.85V) was used for quantitation of the analytes.

The drug-plasma concentration of each sample was calculated by least squares linear regression analysis of the peak-area ratio (parent/internal standard) of the spiked plasma standards versus concentration. The assay was linear over the concentration range 1–533 ng/mL, with a mean percent deviation of <6.5% for the analysis of triplicate standards at seven separate concentrations. The maximum plasma concentration ($C_{max}$) and the time to reach the maximum plasma concentrations ($T_{max}$) were read directly from the observed plasma concentration-time data. The plasma elimination half-life ($T_{1/2}$) was estimated from the log-linear regression of the terminal plasma concentrations as a function of time after dosing. The area under the plasma concentration-time curve was calculated using the linear trapezoidal rule over the single 72-hour dosing interval ($AUC_{0-72}$).

C. Evaluation of In-vivo Drug Release

Four experimental sustained-release suspensions were administered to different groups of three beagle dogs each. Each formulation was evaluated using a 2 mg/kg subcutaneous dose. The plasma concentrations were compared to those obtained from an equivalent dose of the immediate-release injection, Torbugesic-SA. The pharmacokinetic parameters, $C_{max}$, $T_{max}$, $T\frac{1}{2}$, and $AUC_{0-72}$, are given below in Table 7.

Butorphanol was rapidly absorbed from the immediate-release formulation, with the peak concentration (169.3±66.7 nh/mL) recorded one hour after dosing. All four experimental formulations produced a sustained-release profile of butorphanol. The drug-plasma concentration was maintained within the proposed therapeutic window (20–100 ng/mL) over a 24-hour period for the two oil suspensions and the 5 mg/mL aqueous suspension. Also, the time that maximum concentration is reached was relatively fast for all sustained-release formulations. For subcutaneous administration of the aqueous suspensions, the $T_{max}$ was 1.5 and 2.0 hours for the 5 and 10 mg/mL formulations, respectively. A slightly slower absorption was observed for the oil suspensions, with $T_{max}$ values averaging three and four hours for the 10 and 20 mg/mL formulations, respectively. It was also observed that the highest $C_{max}$ and AUC were associated with the 5 mg/mL aqueous suspension.

TABLE 6

Pharmacokinetic Parameter of the Five Formulations

| Formulation | | $C_{max}$ (ng/mL) | $T_{max}$ (hr) | $AUC_{0-72}$ (ng · hr/mL) |
|---|---|---|---|---|
| 5 mg/mL | Mean | 99.7 | 1.5 | 1068.9 |
| Aqueous Suspension | (SEM) | (39.8) | (0.5) | (231.5) |
| 10 mg/mL | Mean | 17.3 | 2.0 | 632.0 |
| Aqueous Suspension | (SEM) | (2.9) | (0.0) | (101.4) |
| 10 mg/mL | Mean | 48.2 | 3.0 | 923.8 |
| Oil Suspension | (SEM) | (1.0) | (1.5) | (134.5) |
| 20 mg/mL | Mean | 33.3 | 4.0 | 698.1 |
| Oil Suspension | (SEM) | (7.5) | (0.0) | (28.4) |
| 2 mg/mL | Mean | 169.3 | 1.0 | 1537.5 |
| Torbugesic-SA | (SEM) | (38.5) | (0.0) | (282.5) |

The data for two oil suspensions and the 5 mg/ml aqueous suspension show a sustained drug-release profile with the drug-plasma concentration maintained within the therapeutic range of 20–80 ng/mL over a 24-hour period of time.

What is claimed is:

1. A method of providing effective pain management over a period of time of at least 12 hours to a human in need of such management comprising injecting into the human an effective amount of a composition comprising butorphanol free base suspended in an aqueous buffer said buffer having a pH less than about 7.0.

2. The method of claim 1 wherein the butorphanol is in the form of microparticles.

3. The method of claim 2 wherein the microparticles have an average diameter of from about 5 to about 25 microns.

4. The method of claim 1 wherein the composition has a pH of from about 6.2 to about 6.5.

5. The method of claim 4 wherein the composition has a pH of from about 6.2 to about 6.3.

6. The method of claim 1 wherein the butorphanol is present in a concentration of from about 4 to about 10 mg/ml.

7. The method of claim 6 wherein the butorphanol is present in a concentration of from about 5 to about 7.5 mg/ml.

8. The method of claim 1 wherein the composition further comprises an effective amount of a non-ionic solubilizing agent.

9. The method of claim 8 wherein the solubilizing agent is a polyoxyethylene sorbitan fatty acid ester.

10. The method of claim 9 wherein the polyoxyethylene sorbitan fatty acid ester is polysorbate 80.

11. The method of claim 1 wherein the composition further comprises an effective amount of a preservative.

12. The method of claim 11 wherein the preservative is an alkylparaben.

13. The method of claim 12 wherein the alkylparaben is methylparaben or propylparaben.

14. The method of claim 1 wherein the period of time is about 12 to about 24 hours.

15. The method of claim 14 wherein the period of time is about 12 to about 18 hours.

16. The method of claim 14 wherein the effective amount is that amount sufficient to maintain plasma butorphanol concentration at a level of between about 20 and 100 ng/ml for a period of time of about 12 to 24 hours.

17. A method of providing effective pain management over a period of time of at least 12 hours to a human in need of such management comprising injecting into the human an effective amount of a composition comprising a butorphanol salt suspended in oil.

18. The method of claim 16 wherein the butorphanol is in the form of microparticles.

19. The method of claim 18 wherein the microparticles have an average diameter of from about 5 to about 25 microns.

20. The method of claim 17 wherein the butorphanol salt is butorphanol tartrate.

21. The method of claim 17 wherein butorphanol is present in a concentration of from about 5 to about 30 mg/ml.

22. The method of claim 21 wherein butorphanol is present in a concentration of from about 10 to about 20 mg/ml.

23. The method of claim 17 wherein the oil is cottonseed oil, corn oil, peanut oil, sesame oil or soybean oil.

24. The method of claim 23 wherein the oil is soybean oil.

25. The method of claim 17 further comprising an effective amount of a suspending agent.

26. The method of claim 25 wherein the suspending agent is a sorbitan fatty acid ester.

27. The method of claim 24 wherein the sorbitan fatty acid ester is Span 85.

28. The method of claim 17 wherein the period of time is about 12 to about 24 hours.

29. The method of claim 28 wherein the period of time is about 18 to about 24 hours.

30. The method of claim 28 wherein the effective amount is that amount sufficient to maintain plasma butorphanol concentration at a level of between about 20 and 100 ng/ml for a period of time of about 12 to 24 hours.

\* \* \* \* \*